United States Patent
Hirayama et al.

[11] Patent Number: 5,919,746
[45] Date of Patent: Jul. 6, 1999

[54] ALKALINE LIPOLYTIC ENZYME

[75] Inventors: Satoshi Hirayama, Chiba, Japan; Torben Halkier, Birkeroed, Denmark

[73] Assignee: Novo Nordisk A/S, Bagsvaerd, Denmark

[21] Appl. No.: 08/919,724

[22] Filed: Aug. 28, 1997

Related U.S. Application Data

[63] Continuation of application No. PCT/DK96/00123, Mar. 27, 1996.

[30] Foreign Application Priority Data

Mar. 30, 1995 [DK] Denmark ................................ 0344/95
Jul. 14, 1995 [DK] Denmark ................................ 0830/95

[51] Int. Cl.$^6$ ............................. C12N 9/20; C11D 3/00; C11D 7/42
[52] U.S. Cl. ......................... 510/392; 435/198; 510/320; 510/321; 510/393
[58] Field of Search ............................ 435/198; 510/392, 510/320, 321, 393

[56] References Cited

U.S. PATENT DOCUMENTS 5,240,851  8/1993  Paridans et al. ...................... 435/253.3

FOREIGN PATENT DOCUMENTS

| | | |
|---|---|---|
| 0 218 272 A1 | 4/1987 | European Pat. Off. . |
| 0 238 023 A2 | 9/1987 | European Pat. Off. . |
| 0 238 023 A3 | 9/1987 | European Pat. Off. . |
| 0 258 068 A2 | 3/1988 | European Pat. Off. . |
| 0 258 068 A3 | 3/1988 | European Pat. Off. . |
| 0 271 152 A2 | 6/1988 | European Pat. Off. . |
| 0 385 401 A1 | 9/1990 | European Pat. Off. . |
| WO 94/14940 | 7/1994 | WIPO . |

OTHER PUBLICATIONS

Derwent Abstract JP04370200 Asahi Pen KK Dec. 22, 1992.
Nucleic Acid Research, Pir. 2, Accession No. Jn0552, Lotti, M. et al., "Cloning and Analysis of Candida Cylindracea Lipase Sequences", Gene 124, 45–55, 1993.
Nucleic Acid Research, Pir. 2, Accession No. S47655, Sone, T. et al., "Cloning And Sequence Analysis Of A Hamster Liver cDNA Encoding A Novel Putative Carboxylesterase". Biochem, Biophys. Acta 1207, 138–142, 1994.
Nucleic Acid research, Pir. 2 Accession No. Jn0553, Lotti, M. et al., "Cloning And Analysis Of Candida Cylindracea Lipase Sequences", Gene 124, 45–55, 1993.
Chemical Abstracts, vol. 95, No. 21, Nov. 23, 1981, The Abstract No. 95: 183581u.
Chemical Abstracts, vol. 92, No. 5, Feb. 4, 1980, The Abstract No. 92: 373376c.

*Primary Examiner*—Herbert J. Lilling
*Attorney, Agent, or Firm*—Steve T. Zelson, Esq.; Valeta Gregg, Esq.

[57] ABSTRACT

The present invention relates to an alkaline lipolytic enzyme derivable from a strain of Botryosphaeria or Guignardia, to a lipolytic enzyme-producing microbial strain, to methods for the production of lipolytic enzyme and to a detergent composition comprising the lipolytic enzyme.

9 Claims, 2 Drawing Sheets

ALKALINE LIPOLYTIC ENZYME

CROSS-REFERENCE TO RELATED APPLICATIONS

This application is a continuation application of PCT/DK96/00123 filed Mar. 27, 1996 which claims priority under 35 U.S.C. 119 of Danish applications 0344/95 and 0830/95 filed Mar. 30, 1995 and Jul. 14, 1995, respectively, the contents of which are fully incorporated herein by reference.

TECHNICAL FIELD

This invention relates to an alkaline lipolytic enzyme, to a lipolytic enzyme-producing microbial strain, to methods for the production of lipolytic enzyme and to a detergent composition comprising the lipolytic enzyme.

BACKGROUND ART

For a number of years lipolytic enzymes have been used as detergent additives to remove lipid or fatty stains from clothes and other textiles.

Thus, the prior art suggests the use of various microbial lipases as detergent additives. Examples include lipases derived from *Humicola lanuginosa* (also called *Thermomyces lanuginosus*, EP 258 068 and EP 305 216), *Rhizomucor miehei* (EP 238 023), *Candida antarctica* (EP 214 761), various species of Pseudomonas such as *P. alcaligenes* and *P. pseudoalcaligenes* (EP 218 272), *P. cepacia* (EP 331 376), Bacillus, e.g. *B. subtilis* (Dartois et al., (1993) Biochemica et Biophysica Acta 1131, 253–260), *B. stearothennophilus* (JP-A 64-74992) and *B. pumilus* (WO 91/16422).

For commercial production of enzymes such as lipases, it is preferred to express the enzyme in a suitable host organism for higher yield. Various expression systems are available, including expression of enzymes from Ascomycetes in Aspergillus (EP 238 023).

Many detergents are alkaline with a high pH in solution (e.g. around pH 10), so there is a need for lipolytic enzymes with high activity at high pH. The lipolytic enzyme should be derived from a type of microorganism for which suitable expression systems are available.

SUMMARY OF THE INVENTION

Surprisingly, we have found that an alkaline lipolytic enzyme can be derived from fungal strains of Botryosphaeria or Guignardia, two closely related genera not previously reported to produce lipolytic enzyme. The novel lipolytic enzyme has optimum activity around pH 10, making it well suited for use in detergents. Advantageously, the microorganisms are Ascomycetes for which suitable expression systems are well developed.

Accordingly, the invention provides a lipolytic enzyme which is derived from a strain of Botryosphaeria or Guignardia or is immunologically reactive with an antibody raised against a purified lipolytic enzyme produced by such strain, and has optimum activity at a pH in the range 9–11 in the presence of 50 mM Ca$^{++}$.

Another aspect of the invention provides an alkaline lipolytic enzyme which contains an amino acid sequence selected from the group consisting of SEQ ID NO: 1, 2, 3, 4 and 5.

The invention also provides novel lipolytic enzyme-producing strains of Botryosphaeria as a biologically pure culture.

In another aspect, the invention provides a process for producing an alkaline lipolytic enzyme, comprising cultivation of a lipolytic enzyme-producing strain of Botryosphaeria or Guignardia in a suitable nutrient medium, followed by recovery of the alkaline lipolytic enzyme.

The invention further provides a method for producing an alkaline lipolytic enzyme, comprising:

a) isolating a DNA fragment encoding the lipolytic enzyme from a lipolytic enzyme-producing strain of Botryosphaeria or Guignardia, b) combining the DNA fragment with appropriate expression signal(s) in an appropriate vector, c) introducing the vector or parts thereof into an appropriate host, d) cultivating the host organism under conditions leading to expression of the lipolytic enzyme, and e) recovering the lipolytic enzyme from the culture medium.

Finally, the invention provides a detergent composition comprising a surfactant together with an effective amount of said lipolytic enzyme.

DETAILED DISCLOSURE OF THE INVENTION

Microorganisms

Figure 1:
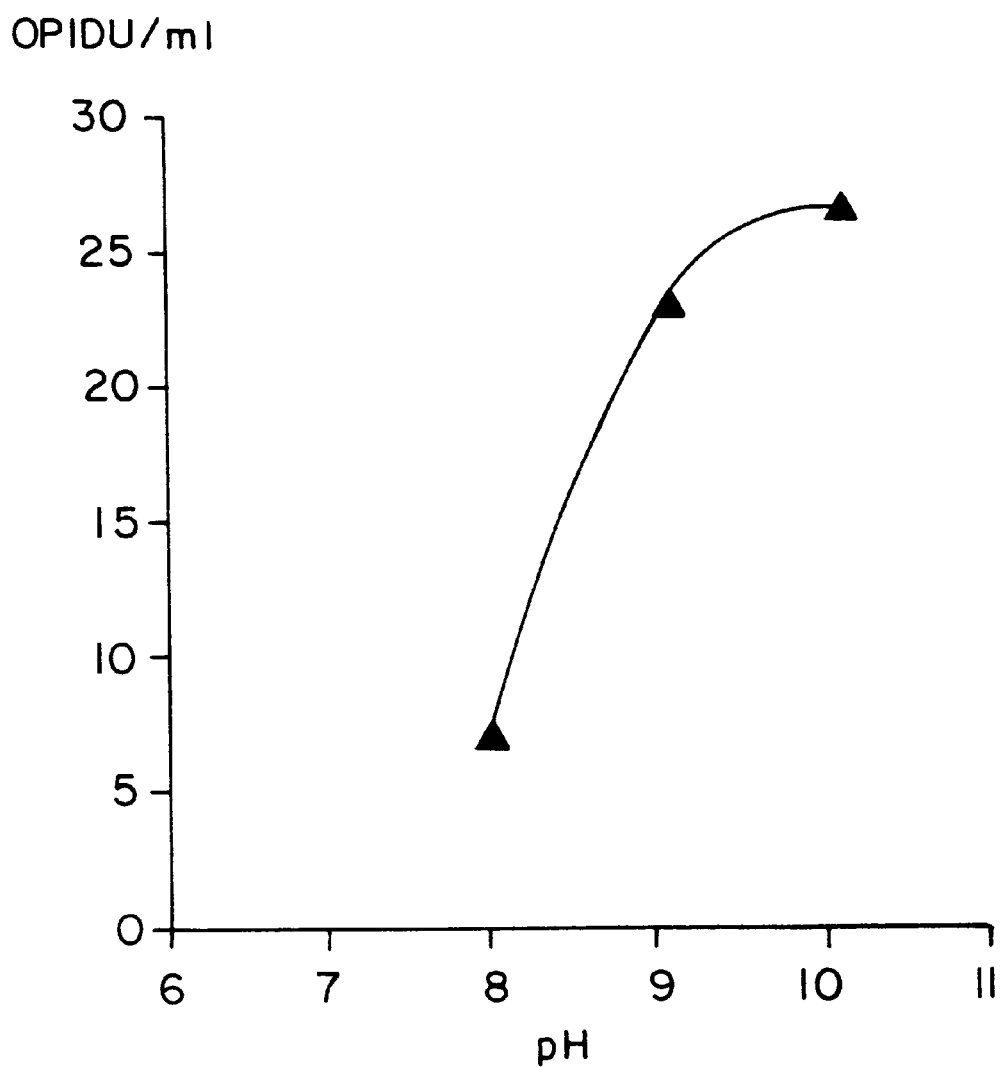
FIGS. 1 and 2 show graphs of lipolytic enzyme activity vs. pH for lipolytic enzymes produced by Botryosphaeria sp. CBS 102.95 and *B. ribis* CBS 504.94, respectively.

The microbial strains used in this invention belong to the genera Botryosphaeria or Guignardia. The two genera are closely related and were considered synonyms by M. E. Barr (Contrib. Univ. Mich. Herb., 9: 523–638, 1972), but most authors consider them separate genera—see for instance A. Sivanesan, J. Cramer, Vaduz, 701 pp, 1984.

Both genera are described by Richard T. Hanlin, Illustrated Genera of Ascomycetes, APS Press, The American Phytopathological Society, St. Paul, Minn., 1990, p. 46–49. The genus Botryosphaeria is also described by Punithalingam, E. & Holliday, P. (1973) *CMI Descriptions of Pathogenic Fungi and Bacteria* No. 395. When cultivated, the strains may develop in the Fusicoccum state or the microconidial state.

Two strains have been isolated and deposited by the inventors according to the Budapest Treaty on the International Recognition of the Deposit of Microorganisms for the Purposes of Patent Procedure at Centraalbureau Voor Schimmelcultures (CBS), Oosterstraat 1, Postbus 273, NL-3740 AG Baarn, Netherlands. The two strains were classified by standard taxonomic methods.

The deposit data and the taxonomic identification of the strains were as follows:

| Depositors' reference | NN143554 | NN115210 |
|---|---|---|
| Deposit number | CBS 102.95 | CBS 504.94 |
| Deposit date | January 6, 1995 | October 19, 1994 |
| Taxonomic designation | Botryosphaeria sp. | *Botryosphaeria ribis* |

Also, the following publicly available strains can be used in the invention:

| Genus | Species | Inventors' strain No. | Deposit number |
|---|---|---|---|
| Botryosphaeria | B. berengeriana | NN102565 | MAFF 06-45001 |
| | B. berengeriana f. sp. pilicola | NN102566 | MAFF 06-45002 |
| | B. dothidea | NN102558 | JCM 2733 |
| | | NN102559 | JCM 2735 |
| | | NN102560 | JCM 2736 |
| | | NN102561 | JCM 2737 |
| | | NN102562 | JCM 2738 |
| | B. parva | NN103321 | ATCC 58191 |
| | B. ribis | NN103322 | ATCC 56125 |
| | B. ribis var. chromogena | NN103313 | CBS 121.26 |
| | B. xanthocephala | NN103324 | ATCC 60638 |
| Guignardia | G. laricina | NN102563 | IFO 7887 |
| | | NN102564 | IFO 7888 |
| | G. paulowniae | NN102567 | MAFF 03-05151 |

The above-mentioned strains are freely available from the following depositary institutions for microorganisms:

MAFF: Ministry of Agriculture, Forestry and Fisheries, National Institute of Agro-Biological Research, 1-2 Kannondai 2-chome, Tsukuba, Ibaraki 305, Japan.

JCM: Japan Collection of Microorganisms, RIKEN, Wako, Saitama 351-01, Japan.

IFO: Institute for Fermentation, Osaka, 17-85, Jusohomnachi 2-chome, Yodogawa-ku, Osaka 532, Japan.

CBS: Centraal Bureau voor Schimmelcultures, Oosterstraat 1, 3740 AG Baarn, Netherlands.

ATCC: American Type Culture Collection, 12301 Parklawn Drive, Rockville, Md. 20852, USA.

Variants and mutants of these strains, capable of producing lipolytic enzyme, may also be used in the invention.

Production of lipolytic enzyme

Lipolytic enzyme may be produced by cultivating any of the microorganisms described above in a suitable nutrient medium, optionally followed by recovery and purification, according to methods well known in the art or as described in the examples of this specification.

The lipolytic enzyme may also be obtained by recombinant DNA-technology by methods known in the art per se, e.g. isolating a DNA fragment encoding the lipolytic enzyme, combining the DNA fragment with appropriate expression signal(s) in an appropriate vector, introducing the vector or parts thereof into an appropriate host (e.g. a filamentous fungus, preferably a member of the genus Aspergillus), either as an autonomously replicating plasmid or integrated into the chromosome, cultivating the host organism under conditions leading to expression of the lipolytic enzyme, and recovering the lipolytic enzyme from the culture medium.

The isolation of a DNA sequence may be done by so-called expression cloning, comprising the following steps:

a) cloning, in suitable vectors, a cDNA library from a lipolytic enzyme-producing strain of Botryosphaeria or Guignardia,
b) transforming suitable yeast host cells with said vectors,
c) cultivating the transformed yeast host cells under suitable conditions to express the alkaline lipolytic enzyme,
d) screening for positive clones by determining the lipolytic enzyme activity expressed in step (c).

The expression cloning may be done as described in WO 93/11249 or in H. Dalbøge and H. P. Heldt-Hansen, *Mol. Gen. Genet.* (1994) 243:253–260. A preferred heterologous host cell is a strain of Aspergillus, e.g. *A. oryzae* or *A. niger*, e.g. using the expression system described in EP-A-0 238 023.

After the cultivation, the lipolytic enzyme may be recovered and purified from the culture broth by conventional methods, such as hydrophobic chromatography, ion exchange chromatography and combinations thereof.

Lipolytic enzymes

The enzymes of this invention are lipolytic enzymes. In the present context the term "lipolytic enzyme" is intended to indicate an enzyme classified under the Enzyme Classification number E.C. 3.1.1.—(Carboxylic Ester Hydrolases) in accordance with the Recommendations (1992) of the International Union of Biochemistry and Molecular Biology (IUBMB). Lipolytic enzymes thus exhibit hydrolytic activity towards at least one of the types of ester bonds mentioned in the context of E.C. 3.1.1. The lipolytic enzymes of the invention preferably have lipase activity (with triglycerides as substrate).

Enzymatic properties

The lipolytic enzymes of this invention are characterized by high activity at alkaline pH. More specifically, they have optimum activity at a pH higher than 9, particularly in the range 9–11, in the presence of 50 mM $Ca^{++}$.

Figure 2:
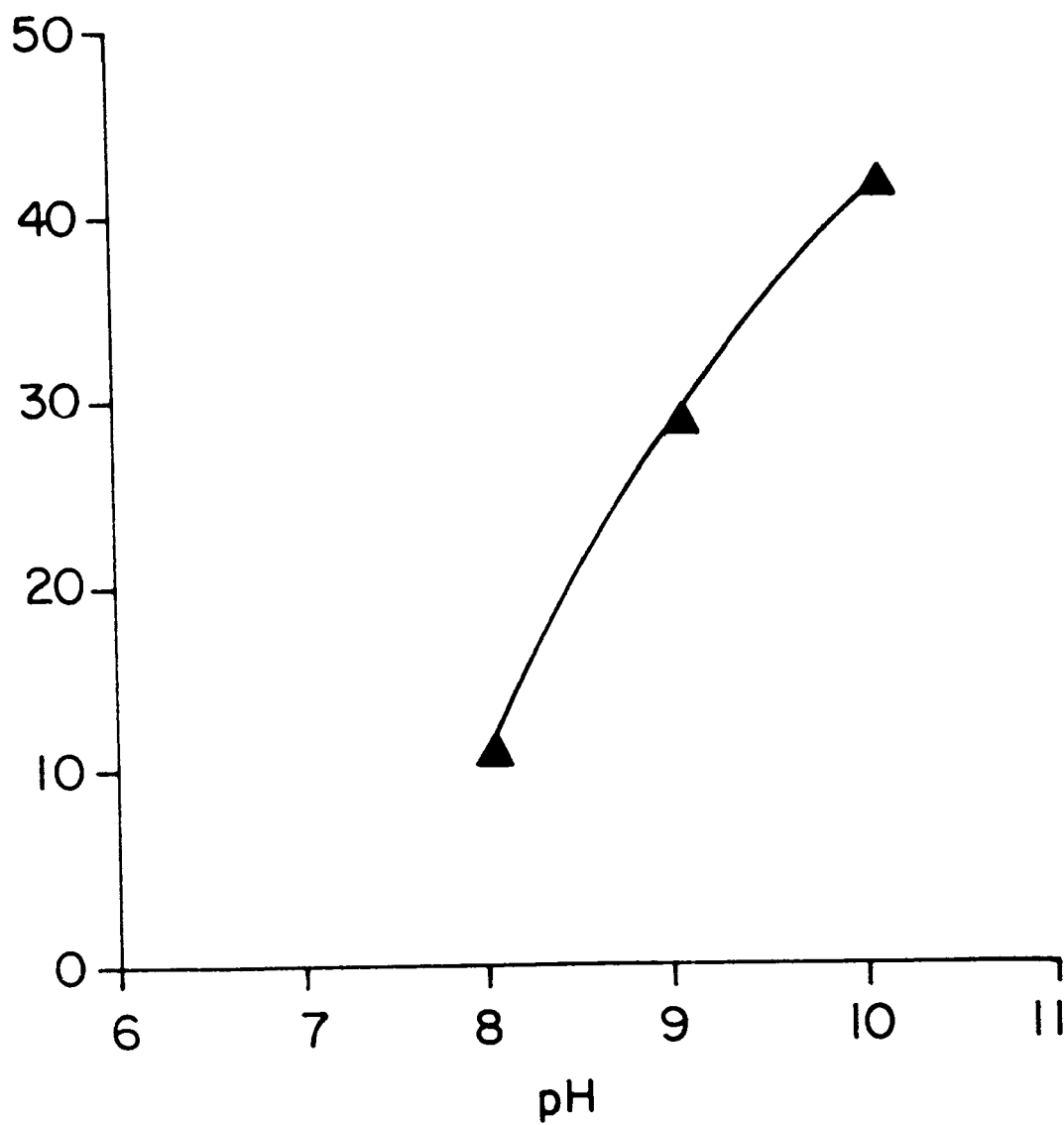

FIGS. 1 and 2 show graphs of lipolytic enzyme activity vs. pH for lipolytic enzymes produced by Botryosphaeria sp. CBS 102.95 and *B. ribis* CBS 504.94, respectively. Both lipolytic enzymes have optimum activity at about pH 10.

The isoelectric point is 3.8 for lipolytic enzyme from CBS 102.95 and 3.4 for lipolytic enzyme from CBS 504.94. The molecular weight is 55,000 Dalton for lipolytic enzyme from CBS 102.95 and 64,000 for lipolytic enzyme from CBS 504.94. The specific lipolytic enzyme activity is 400 $LU/A_{280}$ for lipolytic enzyme from CBS 102.95 and 300 $LU/A_{280}$ for lipolytic enzyme from CBS 504.94 ($A_{280}$=mg of protein determined from absorbance at 280 nm).

One Lipolytic enzyme Unit (LU) is the amount of enzyme which, under standard conditions (i.e. at 30.0° C.; pH 7.0; and tributyrin substrate) liberates 1 μmol of titratable butyric acid per minute.

Immunochemical Properties

Alkaline lipolytic enzymes having immunochemical properties identical or partially identical to those of a lipolytic enzyme native to a strain of Botryosphaeria or Guignardia and having the stated properties are within the scope of the invention.

The immunochemical properties can be determined by immunological cross-reaction identity tests. The identity tests can be performed by the well-known Ouchterlony double immunodiffusion procedure or by tandem crossed immunoelectrophoresis according to I. M. Roitt; Immunology, Gower Medical Publishing (1985) and N. H. Axelsen; Handbook of Immunoprecipitation-in-Gel Techniques, Blackwell Scientific Publications (1983), Chapters 5 and 14. The terms immunochemical identity (antigenic identity) and partial immunochemical identity (partial antigenic identity) are described in Axelsen, supra, Chapters 5, 19 and 20 and Roitt, supra, Chapter 6.

Monospecific antiserum for use in immunological tests can be raised, e.g. in rabbits, against a purified lipolytic enzyme, e.g. as described in Chapter 41 of N. H. Axelsen, supra or Chapter 23 of N. H. Axelsen et al., A Manual of Quantitative Immunoelectrophoresis, Blackwell Scientific Publications (1973).

Detergent additive

According to the invention, the lipolytic enzyme may typically be used as an additive in a detergent composition. This additive is conveniently formulated as a non-dusting granulate, a stabilized liquid, a slurry or a protected enzyme.

A suitable activity range for a detergent additive containing the lipolytic enzyme of this invention is 0.01–100 mg of pure enzyme protein per g of the detergent additive Detergent The lipolytic enzyme of the invention may be incorporated in concentrations conventionally employed in detergents. The amount of lipolytic enzyme protein may be 0.001–10 mg per gram of detergent or 0.001–100 mg per liter of wash liquor.

Detergent Compositions

According to the invention, the lipolytic enzyme may typically be a component of a detergent composition. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethylene glycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

The detergent composition of the invention may be in any convenient form, e.g. as powder, granules, paste or liquid. A liquid detergent may be aqueous, typically containing up to 70% water and 0–30% organic solvent, or nonaqueous.

The detergent composition comprises one or more surfactants, each of which may be anionic, nonionic, cationic, or zwitterionic. The detergent will usually contain 0–50% of anionic surfactant such as linear alkylbenzene sulfonate (LAS), alpha-olefin sulfonate (AOS), alkyl sulfate (fatty alcohol sulfate) (AS), alcohol ethoxysulfate (AEOS or AES), secondary alkane sulfonates (SAS), alpha-sulfo fatty acid methyl esters, alkyl- or alkenylsuccinic acid, or soap. It may also contain 0–40% of nonionic surfactant such as alcohol ethoxylate (AEO or AE), carboxylated alcohol ethoxylates, nonylphenol ethoxylate, alkylpolyglycoside, alkyldimethylamine oxide, ethoxylated fatty acid monoethanolamide, fatty acid monoethanolamide, or polyhydroxy alkyl fatty acid amide (e.g. as described in WO 92/06154).

The detergent composition may additionally comprise one or more other enzymes, such as amylase, cutinase, protease, cellulase, peroxidase, and oxidase, e.g., laccase.

The detergent may contain 1–65 % of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst). The detergent may also be unbuilt, i.e. essentially free of detergent builder.

The detergent may comprise one or more polymers. Examples are carboxymethyl cellulose (CMC), poly(vinyl pyrrolidone) (PVP), polyethylene glycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine (TAED) or nonanoyloxybenzene sulfonate (NOBS). Alternatively, the bleaching system may comprise peroxy acids of, e.g., the amide, imide, or sulfone type.

The enzymes of the detergent composition of the invention may be stabilized using conventional stabilizing agents, e.g. a polyol such as propylene glycol or glycerol, a sugar or sugar alcohol, lactic acid, boric acid, or a boric acid derivative such as, e.g., an aromatic borate ester, and the composition may be formulated as described in, e.g., WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil-redeposition agents, dyes, bactericides, optical brighteners, or perfume.

The pH (measured in aqueous solution at use concentration) will usually be neutral or alkaline, e.g. in the range of 7–11.

Particular forms of detergent compositions within the scope of the invention include:

1) A detergent composition formulated as a granulate having a bulk density of at least 600 g/l comprising

| | |
|---|---|
| Linear alkylbenzenesulfonate (calculated as acid) | 7–12% |
| Alcohol ethoxysulfate (e.g., $C_{12-18}$ alcohol, 1–2 EO) or alkyl sulfate (e.g., $C_{16-18}$) | 1–4% |
| Alcohol ethoxylate (e.g., $C_{14-15}$ alcohol, 7 EO) | 5–9% |
| Sodium carbonate (as $Na_2CO_3$) | 14–20% |
| Soluble silicate (as $Na_2O, 2SiO_2$) | 2–6% |
| Zeolite (as $NaAlSiO_4$) | 15–22% |
| Sodium sulfate (as $Na_2SO_4$) | 0–6% |
| Sodium citrate/citric acid (as $C_6H_5Na_3O_7/C_6H_8O_7$) | 0–15% |
| Sodium perborate (as $NaBO_3.H_2O$) | 11–18% |
| TAED | 2–6% |
| Carboxymethylcellulose | 0–2% |
| Polymers (e.g., maleic/acrylic acid copolymer, PVP, PEG) | 0–3% |
| Enzymes (calculated as pure enzyme protein) | 0.0001–0.1% |
| Minor ingredients (e.g., suds suppressors, perfume, optical brightener, photobleach) | 0–5% |

2) A detergent composition formulated as a granulate having a bulk density of at least 600 g/l comprising

| | |
|---|---|
| Linear alkylbenzenesulfonate (calculated as acid) | 6–11% |
| Alcohol ethoxysulfate (e.g., $C_{12-18}$ alcohol, 1–2 EO) or alkyl sulfate (e.g., $C_{16-18}$) | 1–3% |
| Alcohol ethoxylate (e.g., $C_{14-15}$ alcohol, 7 EO) | 5–9% |
| Sodium carbonate (as $Na_2CO_3$) | 15–21% |
| Soluble silicate (as $Na_2O, 2SiO_2$) | 1–4% |
| Zeolite (as $NaAlSiO_4$) | 24–34% |
| Sodium sulfate (as $Na_2SO_4$) | 4–10% |
| Sodium citrate/citric acid (as $C_6H_5Na_3O_7/C_6H_8O_7$) | 0–15% |
| Carboxymethylcellulose | 0–2% |
| Polymers (e.g., maleic/acrylic acid copolymer, PVP, PEG) | 1–6% |
| Enzymes (calculated as pure enzyme protein) | 0.0001–0.1% |
| Minor ingredients (e.g., suds suppressors, perfume) | 0–5% |

3) A detergent composition formulated as a granulate having a bulk density of at least 600 g/l comprising

| | |
|---|---|
| Linear alkylbenzenesulfonate (calculated as acid) | 5–9% |
| Alcohol ethoxylate (e.g., $C_{12-15}$ alcohol, 7 EO) | 7–14% |
| Soap as fatty acid (e.g., $C_{16-22}$ fatty acid) | 1–3% |
| Sodium carbonate (as $Na_2CO_3$) | 10–17% |
| Soluble silicate (as $Na_2O$, $2SiO_2$) | 3–9% |
| Zeolite (as $NaAlSiO_4$) | 23–33% |
| Sodium sulfate (as Na2SO4) | 0–4% |
| Sodium perborate (as $NaBO_3.H_2O$) | 8–16% |
| TAED | 2–8% |
| Phosphonate (e.g., EDTMPA) | 0–1% |
| Carboxymethylcellulose | 0–2% |
| Polymers (e.g., maleic/acrylic acid copolymer, PVP, PEG) | 0–3% |
| Enzymes (calculated as pure enzyme protein) | 0.0001–0.1% |
| Minor ingredients (e.g., suds suppressors, perfume, optical brightener) | 0–5% |

4) A detergent composition formulated as a granulate having a bulk density of at least 600 g/l comprising

| | |
|---|---|
| Linear alkylbenzenesulfonate (calculated as acid) | 8–12% |
| Alcohol ethoxylate (e.g., $C_{12-15}$ alcohol, 7 EO) | 10–25% |
| Sodium carbonate (as $Na_2CO_3$) | 14–22% |
| Soluble silicate (as $Na_2O$, $2SiO_2$) | 1–5% |
| Zeolite (as $NaAlSiO_4$) | 25–35% |
| Sodium sulfate (as $Na_2SO_4$) | 0–10% |
| Carboxymethylcellulose | 0–2% |
| Polymers (e.g., maleic/acrylic acid copolymer, PVP, PEG) | 1–3% |
| Enzymes (calculated as pure enzyme protein) | 0.0001–0.1% |
| Minor ingredients (e.g., suds suppressors, perfume) | 0–5% |

5) An aqueous liquid detergent composition comprising

| | |
|---|---|
| Linear alkylbenzenesulfonate (calculated as acid) | 15–21% |
| Alcohol ethoxylate (e.g., $C_{12-15}$ alcohol, 7 EO or $C_{12-15}$ alcohol, 5 EO) | 12–18% |
| Soap as fatty acid (e.g., oleic acid) | 3–13% |
| Alkenylsuccinic acid ($C_{12-14}$) | 0–13% |
| Aminoethanol | 8–18% |
| Citric acid | 2–8% |
| Phosphonate | 0–3% |
| Polymers (e.g., PVP, PEG) | 0–3% |
| Borate (as $B_4O_7$) | 0–2% |
| Ethanol | 0–3% |
| Propylene glycol | 8–14% |
| Enzymes (calculated as pure enzyme protein) | 0.0001–0.1% |
| Minor ingredients (e.g., dispersants, suds suppressors, perfume, optical brightener) | 0–5% |

6) An aqueous structured liquid detergent composition comprising

| | |
|---|---|
| Linear alkylbenzenesulfonate (calculated as acid) | 15–21% |
| Alcohol ethoxylate (e.g., $C_{12-15}$ alcohol, 7 EO, or $C_{12-15}$ alcohol, 5 EO) | 3–9% |
| Soap as fatty acid (e.g., oleic acid) | 3–10% |
| Zeolite (as $NaAlSiO_4$) | 14–22% |
| Potassium citrate | 9–18% |
| Borate (as $B_4O_7$) | 0–2% |
| Carboxymethylcellulose | 0–2% |
| Polymers (e.g., PEG, PVP) | 0–3% |
| Anchoring polymers such as, e.g., lauryl methacrylate/acrylic acid copolymer; molar ratio 25:1; MW 3800 | 0–3% |
| Glycerol | 0–5% |
| Enzymes (calculated as pure enzyme protein) | 0.0001–0.1% |
| Minor ingredients (e.g., dispersants, suds suppressors, perfume, optical brighteners) | 0–5% |

7) A detergent composition formulated as a granulate having a bulk density of at least 600 g/l comprising

| | |
|---|---|
| Fatty alcohol sulfate | 5–10% |
| Ethoxylated fatty acid monoethanolamide | 3–9% |
| Soap as fatty acid | 0–3% |
| Sodium carbonate (as $Na_2CO_3$) | 5–10% |
| Soluble silicate (as $Na_2O$, $2SiO_2$) | 1–4% |
| Zeolite (as $NaAlSiO_4$) | 20–40% |
| Sodium sulfate (as $Na_2SO_4$) | 2–8% |
| Sodium perborate (as $NaBO_3.H_2O$) | 12–18% |
| TAED | 2–7% |
| Polymers (e.g., maleic/acrylic acid copolymer, PEG) | 1–5% |
| Enzymes (calculated as pure enzyme protein) | 0.0001–0.1% |
| Minor ingredients (e.g., optical brightener, suds suppressors, perfume) | 0–5% |

8) A detergent composition formulated as a granulate comprising

| | |
|---|---|
| Linear alkylbenzenesulfonate (calculated as acid) | 8–14% |
| Ethoxylated fatty acid monoethanolamide | 5–11% |
| Soap as fatty acid | 0–3% |
| Sodium carbonate (as $Na_2CO_3$) | 4–10% |
| Soluble silicate (as $Na_2O$, $2SiO_2$) | 1–4% |
| Zeolite (as $NaAlSiO_4$) | 30–50% |
| Sodium sulfate (as $Na_2SO_4$) | 3–11% |
| Sodium citrate (as $C_6H_5Na_3O_7$) | 5–12% |
| Polymers (e.g., PVP, maleic/acrylic acid copolymer, PEG) | 1–5% |
| Enzymes (calculated as pure enzyme protein) | 0.0001–0.1% |
| Minor ingredients (e.g., suds suppressors, perfume) | 0–5% |

9) A detergent composition formulated as a granulate comprising

| | |
|---|---|
| Linear alkylbenzenesulfonate (calculated as acid) | 6–12% |
| Nonionic surfactant | 1–4% |
| Soap as fatty acid | 2–6% |
| Sodium carbonate (as $Na_2CO_3$) | 14–22% |
| Zeolite (as $NaAlSiO_4$) | 18–32% |
| Sodium sulfate (as $Na_2SO_4$) | 5–20% |
| Sodium citrate (as $C_6H_5Na_3O_7$) | 3–8% |
| Sodium perborate (as $NaBO_3.H_2O$) | 4–9% |
| Bleach activator (e.g., NOBS or TAED) | 1–5% |
| Carboxymethylcellulose | 0–2% |
| Polymers (e.g., polycarboxylate or PEG) | 1–5% |
| Enzymes (calculated as pure enzyme protein) | 0.0001–0.1% |
| Minor ingredients (e.g., optical brightener, perfume) | 0–5% |

10) An aqueous liquid detergent composition comprising

| | |
|---|---|
| Linear alkylbenzenesulfonate (calculated as acid) | 15–23% |
| Alcohol ethoxysulfate (e.g., $C_{12-15}$ alcohol, 2–3 EO) | 8–15% |
| Alcohol ethoxylate (e.g., $C_{12-15}$ alcohol, 7 EO, or $C_{12-15}$ alcohol, 5 EO) | 3–9% |
| Soap as fatty acid (e.g., lauric acid) | 0–3% |
| Aminoethanol | 1–5% |
| Sodium citrate | 5–10% |
| Hydrotrope (e.g., sodium toluensulfonate) | 2–6% |
| Borate (as $B_4O_7$) | 0–2% |
| Carboxymethylcellulose | 0–1% |
| Ethanol | 1–3% |
| Propylene glycol | 2–5% |
| Enzymes (calculated as pure enzyme protein) | 0.0001–0.1% |
| Minor ingredients (e.g., polymers, dispersants, perfume, optical brighteners) | 0–5% |

11) An aqueous liquid detergent composition comprising

| | |
|---|---|
| Linear alkylbenzenesulfonate (calculated as acid) | 20–32% |
| Alcohol ethoxylate (e.g., $C_{12-15}$ alcohol, 7 EO, or $C_{12-15}$ alcohol, 5 EO) | 6–12% |
| Aminoethanol | 2–6% |
| Citric acid | 8–14% |
| Borate (as $B_4O_7$) | 1–3% |
| Polymer (e.g., maleic/acrylic acid copolymer, anchoring polymer such as, e.g., lauryl methacrylate/acrylic acid copolymer) | 0–3% |
| Glycerol | 3–8% |
| Enzymes (calculated as pure enzyme protein) | 0.0001–0.1% |
| Minor ingredients (e.g., hydrotropes, dispersants, perfume, optical brighteners) | 0–5% |

12) A detergent composition formulated as a granulate having a bulk density of at least 600 g/l comprising

| | |
|---|---|
| Anionic surfactant (linear alkylbenzenesulfonate, alkyl sulfate, alpha-olefinsulfonate, alpha-sulfo fatty acid methyl esters, alkanesulfonates, soap) | 25–40% |
| Nonionic surfactant (e.g., alcohol ethoxylate) | 1–10% |
| Sodium carbonate (as $Na_2CO_3$) | 8–25% |
| Soluble silicates (as $Na_2O, 2SiO_2$) | 5–15% |
| Sodium sulfate (as $Na_2SO_4$) | 0–5% |
| Zeolite (as $NaAlSiO_4$) | 15–28% |
| Sodium perborate (as $NaBO_3.4H_2O$) | 0–20% |
| Bleach activator (TAED or NOBS) | 0–5% |
| Enzymes (calculated as pure enzyme protein) | 0.0001–0.1% |
| Minor ingredients (e.g., perfume, optical brighteners) | 0–3% |

13) Detergent compositions as described in compositions 1–12 wherein all or part of the linear alkylbenzenesulfonate is replaced by ($C_{12}$–$C_{18}$) alkyl sulfate.

14) A detergent composition formulated as a granulate having a bulk density of at least 600 g/l comprising

| | |
|---|---|
| ($C_{12}$–$C_{18}$) alkyl sulfate | 9–15% |
| Alcohol ethoxylate | 3–6% |
| Polyhydroxy alkyl fatty acid amide | 1–5% |
| Zeolite (as $NaAlSiO_4$) | 10–20% |
| Layered disilicate (e.g., SK56 from Hoechst) | 10–20% |
| Sodium carbonate (as $Na_2CO_3$) | 3–12% |
| Soluble silicate (as $Na_2O, 2SiO_2$) | 0–6% |
| Sodium citrate | 4–8% |
| Sodium percarbonate | 13–22% |
| TAED | 3–8% |
| Polymers (e.g., polycarboxylates and PVP) | 0–5% |
| Enzymes (calculated as pure enzyme protein) | 0.0001–0.1% |
| Minor ingredients (e.g., optical brightener, photo bleach, perfume, suds suppressors) | 0–5% |

15) A detergent composition formulated as a granulate having a bulk density of at least 600 g/l comprising

| | |
|---|---|
| ($C_{12}$–$C_{18}$) alkyl sulfate | 4–8% |
| Alcohol ethoxylate | 11–15% |
| Soap | 1–4% |
| Zeolite MAP or zeolite A | 35–45% |
| Sodium carbonate (as $Na_2CO_3$) | 2–8% |
| Soluble silicate (as $Na_2O, 2SiO_2$) | 0–4% |
| Sodium percarbonate | 13–22% |
| TAED | 1–8% |
| Carboxymethyl cellulose | 0–3% |
| Polymers (e.g., polycarboxylates and PVP) | 0–3% |
| Enzymes (calculated as pure enzyme protein) | 0.0001–0.1% |
| Minor ingredients (e.g., optical brightener, phosphonate, perfume) | 0–3% |

16) Detergent compositions as described in compositions 1–15 which contain a stabilized or encapsulated peracid, either as an additional component or as a substitute for already specified bleach systems.

17) Detergent compositions as described in compositions 1, 3, 7, 9 and 12 wherein perborate is replaced by percarbonate.

18) Detergent compositions as described in 1), 3), 7), 9), 12), 14) and 15) which additionally contain a manganese catalyst. The manganese catalyst may, e.g., be one of the compounds described in "Efficient manganese catalysts for low-temperature bleaching", *Nature* 369, 1994, pp. 637–639.

19) Detergent composition formulated as a nonaqueous detergent liquid comprising a liquid nonionic surfactant such as, e.g., linear alkoxylated primary alcohol, a builder system (e.g. phosphate), enzyme and alkali. The detergent may also comprise anionic surfactant and/or a bleach system.

The lipolytic enzyme of the invention may be incorporated in concentrations conventionally employed in detergents. It is at present contemplated that, in the detergent composition of the invention, the lipolytic enzyme may be added in an amount corresponding to 0.00001–1 mg (calculated as pure enzyme protein) of lipolytic enzyme per liter of wash liquor.

EXAMPLES

Example 1

Production of lipolytic enzyme from Botryosphaeria sp.
The following media were used in this example:

| Medium | YS-2 | YS-25 |
|---|---|---|
| pH | 6.5 | 6.5 |
| Glucose | 20 g/L | 5 g/L |
| Yeast extract | 10 g/L | 10 g/L |
| Peptone | 10 g/L | 10 g/L |
| $K_2HPO_4$ | 5 g/L | 5 g/L |
| $MgSO_4 7H_2O$ | 1 g/L | 1 g/L |
| Soybean oil | 0 | 2 ml/100 ml |

A seed culture was prepared by inoculating strain CBS 102.95 from a slant of PDA (product of Difco) to two shake flasks containing 100 ml of YS-2 medium, and incubating the shake flasks with shaking for 2 days at 27° C. The final pH was 7.5.

A main culture was prepared by using the seed culture to inoculate 50 shake flasks with 100 ml of YS-25 medium and incubating for 2 days at 27° C. with shaking. The final pH was 7.3.

2,900 ml of cell-free broth with a lipolytic enzyme activity of 17 LU/ml was recovered after removal of the cell mass. This was deionized and freeze-dried to obtain 11.9 g of powder sample with a lipolytic enzyme activity of 3,540 LU/g.

Example 2

Production of lipolytic enzyme from *Botryosphaeria ribis*

Lipolytic enzyme was produced in the same manner as in Example 1, except that strain CBS 504.94 was used, and 3 days were used for the main culture. A cell-free broth with a lipolytic enzyme activity of 10 LU/ml was recovered after removal of the cell mass. This was deionized and freeze-dried to obtain 17.8 g of powder sample with a lipolytic enzyme activity of 3,050 LU/g.

Example 3
Purification and characterization of lipolytic enzyme from Botryosphaeria sp.

Purification procedure

Crude lipolytic enzyme from Botryosphaeria sp. CBS 102.95 was purified using a 2-step protocol using anion exchange and hydrophobic chromatography, as follows.

Anion exchange chromatography 6.2 g of the lipolytic enzyme preparation from Example 1 was dissolved in 10 mM Tris-HCl, pH 7 and dialyzed against the same buffer. The solution was applied onto a column packed with Q Sepharose (product of Pharmacia) equilibrated with the same buffer at a flow rate of 5 ml/min. Unbound material was washed with the same buffer, and the lipolytic enzyme was eluted with a linear gradient of 0–1M NaCl concentration in the same buffer. Obtained fractions were assayed for lipolytic enzyme activity and pooled. The yield of this step was 54%.

Hydrophobic chromatography

To the lipolytic enzyme pool, ammonium acetate was added to give a final concentration of 0.8M. The solution was applied to a column packed with Butyl Sepharose (product of Pharmacia) previously equilibrated with 0.8M ammonium acetate. After thoroughly washing with a large amount of the same buffer, elution was done firstly with milli-Q-water and secondly with 30% isopropanol. The water fraction contained 59% of the applied activity, and the isopropanol fraction contained 27%.

Summary of the purification

| Step | Activity (LU) | Yield (%) |
| --- | --- | --- |
| Powder | 22,000 | 100 |
| Q Sepharose | 11,850 | 54 |
| Butyl Sepharose water pool | 6,990 | 32 |
| isopropanol pool | 3,200 | 15 |

Characterization

Purity and molecular weight of the lipolytic enzyme were analyzed using a 4.20% gradient SDS-PAGE gel (Novex) under standard conditions. Molecular weight marker proteins were purchased from Pharmacia. After electrophoresis, proteins were stained with Coomassie brilliant blue. The molecular weight of the lipolytic enzyme from both the water pool and the isopropanol were found to be 55,000.

The pI of the lipolytic enzyme was measured using Ampholine PAG plate, pH 3.5–9.5 (product of Pharmacia). pI marker proteins from Pharmacia were used. The pI of the lipolytic enzyme from both pools was pI 3.8.

These results indicated that the lipolytic enzyme from the two pools obtained from Butyl Sepharose is the same. The lipolytic enzyme from the water pool was chosen for use in the characterization due to the higher purity.

The specific activity of the lipolytic enzyme was found to be about 400 LU/$A_{280}$ (protein content determined by absorbance at 280 nm).

Example 4
Purification and characterization of lipolytic enzyme from *Botryosphaeria ribis*

Purification procedure

Crude lipolytic enzyme from *Botryosphaeria ribis* CBS 504.94 was purified by 3 steps as follows.

STREAM LINE™ column chromatography

The first step was STREAM LINE column chromatography. 14.3 g of the freeze-dried powder from Example 2 and 3.5 g of a another freeze-dried powder (made in essentially the same manner as in Example 2 and having a lipolytic enzyme activity of 1780 LU/g) were dissolved in 50 mM Tris-HCl buffer (pH 7.6). The lipolytic enzyme was adsorbed on a column of DEAE resin equilibrated with the same buffer, and the column was washed with the same buffer. The lipolytic enzyme was eluted with the same buffer including 0.5M NaCl. The yield of this step was 45%.

Hydrophobic column chromatography

The second step was hydrophobic column chromatography using pre-packed Butyl Toyopearl (product of Toyo Soda) and HPLC. The concentrated lipolytic enzyme was adjusted to a salt concentration of 1M ammonium acetate. Elution was carried out by a linear gradient of 1-0M ammonium acetate and 20% ethanol. The fractions showing lipolytic enzyme activity were gathered. Ultrafiltration was performed to concentrate and desalt. The yield of this step was 89%.

Anion exchange column chromatography

The third step was anion exchange column chromatography using pre-packed DEAE Toyopearl (product of Toyo Soda). The lipolytic enzyme was adjusted to pH 7.6 and 0.1M NaCl. This was applied to the column equilibrated with 50 mM Tris-HCl buffer (pH 7.6) including 0.1M NaCl, and the lipolytic enzyme was eluted with a linear gradient of 0.1–2M NaCl. The chromatogram showed two peaks with lipolytic enzyme activity. The fractions corresponding to the first peak were gathered and dialyzed for use in characterization of the lipolytic enzyme.

Summary of purification

| Step | Activity (LU) | Yield (%) | |
| --- | --- | --- | --- |
| Powder | 64615 | | 100 |
| STREAM LINE | 29070 | 44.9 | 44.9 |
| Butyl Toyopearl | 26814 | 92.2 | 41.4 |
| DEAE Toyopearl | 4984 | 18.6 | 7.7 |

Molecular weight

The molecular weight of the purified lipolytic enzyme was calculated by SDS-PAGE and gel filtration column chromatography. SDS-PAGE was carried out using a 10–15 gradient gel (product of Pharmacia) and Phast System™ under standard conditions. Molecular weight marker proteins were purchased from Pharmacia. After hydrolysis, proteins were stained with Coomassie brilliant blue. The molecular weight of the lipolytic enzyme was found to be 64,000.

Gel filtration chromatography was carried out with Superdex 200pg 26/60 (product of Pharmacia) and HPLC. 2 ml of purified lipolytic enzyme was applied onto the column equilibrated with 50 mM Tris-HCl buffer including 0.1M NaCl, and lipolytic enzyme was eluted with the same buffer. The flow rate was 3 ml/min. Gel Filtration Calibration Kit (product of Pharmacia) was used as the standard proteins. The molecular weight was found to be 54,000.

Iso-electric point

The pI of the lipolytic enzyme was determined by IEF-PAGE using a 3–9 gradient gel and Phast System™. pI marker proteins from Pharmacia were used. After electrophoresis, there was one band below pH 3.5 with the Coomassie brilliant blue staining. The lipolytic enzyme activity was found at the same position using olive oil emulsion and brilliant green.

Specific activity

The specific activity was found to be about 300 LU/mg. The protein amount was measured by protein assay kit, and Bovine Plasma Globulin Lyophilized was used as standard (product of Bio-Rad).

Example 5
Production of lipolytic enzyme from various strains

Each of the strains listed below was cultivated on an agar slant. About 1 cm² of the slant culture was scraped off and used to inoculate 100 ml of YS-2 medium in 500 ml shake flasks with two baffles. This seed culture was incubated at 30° C. with shaking (approx. 220 rpm) for 2 days.

A main culture was prepared by inoculating 3 ml of the seed culture into 100 ml of YS-25 in 500 ml shake flasks with two baffles and cultivating at 30° C with shaking (approx. 220 rpm). The cultivation was continued for 3 days, except that it was extended to 6 days for the strains NN102563 and NN102564 because they were observed to grow more slowly than the other strains. At the end of cultivation, the lipolytic enzyme activity of the broth was measured.

Each experiment was carried out twice, and the results (average of the two experiments) were as follows:

| Species | Strain No. | Lipolytic enzyme activity (LU/ml) |
| --- | --- | --- |
| B. dothidea | NN102558 | 1.5 |
| B. dothidea | NN102559 | 1.6 |
| B. dothidea | NN102560 | 1.4 |
| B. dothidea | NN102561 | 1.4 |
| B. dothidea | NN102562 | 14.5 |
| G. laricina | NN102563 | 0.2 |
| G. laricina | NN102564 | 1.4 |
| B. berengeriana | NN102565 | 1.1 |
| B. berengeriana f. sp. pilicola | NN102566 | 1.3 |
| G. paulowniae | NN102567 | 5.3 |
| Botryosphaeria sp. | NN143554 | 27.0 |
| B. ribis | NN115210 | 4.8 |
| B. parva | NN103321 | 4.8 |
| B. ribis | NN103322 | 1.7 |
| B. ribis var. chromogena | NN103313 | 4.2 |
| B. xanthocephala | NN103324 | 3.3 |

It is seen that lipolytic enzyme could be obtained from all the strains tested. It is further seen that the yield with the strain Botryosphaeria NN143554 (CBS 102.95) which was isolated by the inventors is remarkably higher than with other strains.

Example 6
Plate test for lipolytic enzyme activity at pH 10

The plate test described in Example 11 of WO 88/02775 (corresponding to JP-W 1-501120) was used to check for lipolytic enzyme activity at pH 10 with and without the addition of $Ca^{++}$, using culture broth from the previous example. The samples from all strains tested in Example 5 were found to exhibit lipolytic enzyme activity at pH 10, both with and without $Ca^{++}$ addition.

Example 7
Determination of partial amino acid sequences

Purified lipases from B. ribis NN115210 and Botryosphaeria sp. NN143554 were subjected to sequencing.

No N-terminal amino acid sequences were obtained by direct sequencing of the two lipases. This shows that the N-terminal amino-group is blocked.

The two lipases were reduced and S-carboxymethylated before degradation with a lysyl-specific protease. The resulting peptides were fractionated and repurified using reversed phase HPLC before subjected to N-terminal amino acid sequencing.

5 peptide sequences were obtained from the NN115210 lipase. They are shown in the sequence listings as SEQ ID NO: 1 to 5.

The Xaa residue in SEQ ID NO: 4 is probably a glycosylated Asn residue.

One peptide sequence was obtained from the NN143554 lipase. This amino acid sequence was identical to the amino acid sequence shown in SEQ ID NO: 1 from the NN115210 lipase.

The peptide sequences were aligned to the known sequence of the lipase LIP 1 from *Candida cylindracea* CBS 6330 which has 534 amino acids. The five peptides were found to align to the following positions of LIP 1. The number of matching amino acids and the total amino acids in the peptide are given in parentheses. A gap was inserted between positions 373–374 of the LIP 1 sequence to improve the alignment.

SEQ ID NO: 1: positions 35–47 (12/13)

SEQ ID NO: 2: positions 148–187 (22/40)

SEQ ID NO: 3: positions 255–276 (7/22)

SEQ ID NO: 4: positions 296–331 (11/36)

SEQ ID NO: 5: positions 365–403 (18/40, gap inserted)

Based on this alignment, it is believed that the 5 peptides are partial sequences occurring in this order.

We claim:

1. An alkaline lipolytic enzyme isolated from a strain of Botryosphaeria or Guignardia,
    (a) has optimum activity at a pH in the range 9–11 in the presence of 50 mM $Ca^{++}$, and
    (b) contains an amino acid sequence selected from the group consisting of SEQ ID NO: 2, 3, 4 and 5.

2. The lipolytic enzyme of claim 1 wherein the strain belongs to Botryosphaeria.

3. The lipolytic enzyme of claim 2, wherein the Botryosphaeria strain is one of *B. berengeriana, B. berengeriana f. sp. pilicola, B. dothidea, B. parva, B. ribis, B. ribis var. chromogena* or *B. xanthocephala*.

4. The lipolytic enzyme of claim 1 wherein the strain is *G. laricina* or *G. paulowniae*.

5. The lipolytic enzyme of claim 4 wherein the strain is *G. laricina* IFO 7887, IFO 7888 or *G. paulowniae* MAFF 03-05151.

6. The lipolytic enzyme of claim 1 wherein the sequence contains all of said sequences.

7. The lipolytic enzyme of claim 1 provided as a detergent additive in the form of a non-dusting granulate, a stabilized liquid, a slurry, or a protected enzyme.

8. A detergent composition comprising a surfactant and the alkaline lipolytic enzyme of claim 1.

9. The lipolytic enzyme of claim 3 wherein the strain is *B. berengeriana* MAFF 0645001, *B. berengeriana f. sp. pilicola* MAFF 06-4,5002, *B. dothidea* JCM 2733, JCM 2735, JCM 2736, JCM 2737, JCM 2738, *B. parva* ATCC 58191, *B. ribis* CBS 504.94, ATCC 56125, *B. ribis var. chromogena* CBS 121.26, *B. xanthocephala* ATCC 60638 or Botryosphaeria sp. CBS 102.95.

* * * * *

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 13 amino acids
      (B) TYPE: amino acid
      (C) STRANDEDNESS: single
      (D) TOPOLOGY: linear (ii) MOLECULE TYPE: peptide (v) FRAGMENT TYPE: internal (vi) ORIGINAL SOURCE:
      (A) ORGANISM: Botryosphaeria ribis
      (B) STRAIN: CBS 504.94

(xi) SEQUENCE DESCRIPTION: SEQ ID NO: 1:

Gly Ile Pro Phe Ala Gln Pro Pro Val Gly Pro Leu Arg
1               5                   10

(2) INFORMATION FOR SEQ ID NO: 2:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Botryosphaeria ribis
        (B) STRAIN: CBS 504.94

(xi) SEQUENCE DESCRIPTION: SEQ ID NO: 2:

Asp Ile Ile Phe Val Ala Val Asn Tyr Arg Val Gly Gly Phe Gly Phe
1               5                   10                  15

Leu Pro Gly Glu Glu Leu Gln Arg Asp Gly Ser Thr Asn Leu Gly Leu
                20                  25                  30

Arg Asp Gln Arg Leu Ala Leu Glu
            35                  40

(2) INFORMATION FOR SEQ ID NO: 3:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Botryosphaeria ribis
        (B) STRAIN: CBS 504.94

(xi) SEQUENCE DESCRIPTION: SEQ ID NO: 3:

Ala Gln Asn Ile Tyr Asn Thr Val Val Glu Ser Ala Gly Cys Ser Gly
1               5                   10                  15

Ser Ser Asp Thr Leu Asn
                20

(2) INFORMATION FOR SEQ ID NO: 4:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Botryosphaeria ribis
        (B) STRAIN: CBS 504.94

(xi) SEQUENCE DESCRIPTION: SEQ ID NO: 4:

Ile Phe Gly Tyr Arg Ser Leu Asp Leu Ser Tyr Leu Pro Arg Pro Asp
1               5                   10                  15

-continued

```
Pro Ser Asp Asn Phe Tyr Ser Glu Ser Pro Asp Val Xaa Val Thr Ala
            20                  25                  30

Gly Arg Phe Ala
        35
```

(2) INFORMATION FOR SEQ ID NO: 5:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: peptide (v) FRAGMENT TYPE: internal (vi) ORIGINAL SOURCE:
        (A) ORGANISM: Botryosphaeria ribis
        (B) STRAIN: CBS 504.94

(xi) SEQUENCE DESCRIPTION: SEQ ID NO: 5:

```
Ser Tyr Phe Pro Ala Thr Asp Pro Gln Val Val Ala Asp Leu Val Ala
1               5                   10                  15

Ser Tyr Pro Asn Asn Ile Pro Ala Gly Ser Pro Phe Arg Thr Gly Val
            20                  25                  30

Leu Asn Glu Ile Arg Pro Gln Phe
        35                  40
```